United States Patent
Ueda et al.

(10) Patent No.: US 10,094,609 B2
(45) Date of Patent: Oct. 9, 2018

(54) REFRIGERANT PACK

(71) Applicant: Toppan Farms Co., Ltd., Tokyo (JP)

(72) Inventors: Nobutaka Ueda, Tokyo (JP); Yasuhiro Tanaka, Tokyo (JP)

(73) Assignee: TOPPAN FORMS CO., LTD., Tokyo (JP)

( * ) Notice: Subject to any disclaimer, the term of this patent is extended or adjusted under 35 U.S.C. 154(b) by 227 days.

(21) Appl. No.: 15/124,585

(22) PCT Filed: Feb. 26, 2015

(86) PCT No.: PCT/JP2015/055677
§ 371 (c)(1),
(2) Date: Sep. 8, 2016

(87) PCT Pub. No.: WO2015/141436
PCT Pub. Date: Sep. 24, 2015

(65) Prior Publication Data
US 2017/0023288 A1 Jan. 26, 2017

(30) Foreign Application Priority Data

Mar. 20, 2014 (JP) ................................. 2014-058988
Feb. 25, 2015 (JP) ................................. 2015-035458

(51) Int. Cl.
| | | |
|---|---|---|
| *C09K 5/06* | (2006.01) | |
| *F25D 3/00* | (2006.01) | |
| *C09K 5/08* | (2006.01) | |
| *G01N 21/80* | (2006.01) | |
| *G01N 31/22* | (2006.01) | |

(52) U.S. Cl.
CPC ................ *F25D 3/00* (2013.01); *C09K 5/066* (2013.01); *C09K 5/08* (2013.01); *G01N 21/80* (2013.01); *G01N 31/221* (2013.01); *G01N 31/229* (2013.01)

(58) Field of Classification Search
CPC .. F25D 3/00; C09K 5/066; C09K 5/08; G01N 21/80; G01N 31/221; G01N 31/229
See application file for complete search history.

(56) References Cited

U.S. PATENT DOCUMENTS

| | | | | |
|---|---|---|---|---|
| 4,081,256 A | * | 3/1978 | Donnelly ............... | C09K 5/066 252/70 |
| 4,780,117 A | * | 10/1988 | Lahey ..................... | A61F 7/106 126/263.07 |
| 5,261,241 A | | 11/1993 | Kitahara et al. | |
| 2003/0070436 A1 | * | 4/2003 | Wood ..................... | C09K 5/066 62/114 |
| 2008/0207794 A1 | * | 8/2008 | Wright ..................... | D01D 5/00 522/183 |

FOREIGN PATENT DOCUMENTS

| | | |
|---|---|---|
| CN | 103242806 A | 8/2013 |
| JP | 01-058074 A | 4/1989 |
| JP | 04-239091 A | 8/1992 |
| JP | 2002-129153 A | 5/2002 |
| JP | 2005-283382 A | 10/2005 |
| JP | 2006-097984 A | 4/2006 |
| JP | 2011133202 A | 7/2011 |
| TW | 252147 B | 7/1995 |
| WO | WO2014050157 A1 | 4/2014 |

OTHER PUBLICATIONS

International Search Report for PCT/JP2015/055677, pp. 1-4, dated May 19, 2015.
Office Action from corresponding Taiwan Application No. 104106292, pp. 1-4, dated May 14, 2018.

* cited by examiner

*Primary Examiner* — John R Hardee
(74) *Attorney, Agent, or Firm* — Hoffmann & Baron, LLP

(57) ABSTRACT

A refrigerant pack is provided with a refrigerant substance containing water, a precipitating component, a non-precipitating component, and a pH indicator, and is configured such that the precipitating component precipitates when the refrigerant substance freezes and is a component not corresponding to the pH indicator, the non-precipitating component does not precipitate when the refrigerant substance freezes and is a component not corresponding to the pH indicator, a change or the presence/absence of coloring in the pH indicator is reflected before and after freezing, and the refrigerant substance changes in color.

6 Claims, No Drawings

REFRIGERANT PACK

TECHNICAL FIELD

The present invention relates to a refrigerant pack provided with a refrigerant substance in which a color change when cooling can be easily visually recognized.

Priority is claimed on Japanese Patent Application No. 2014-058988, filed Mar. 20, 2014, and Japanese Patent Application No. 2015-35458, filed Feb. 25, 2015, the contents of which are incorporated herein by reference.

BACKGROUND ART

A refrigerant pack is widely used for cooling at the time of storage or transportation of various fresh products, and typically, this is repeatedly used. The refrigerant pack is provided with a refrigerant substance having a cooling action, and is configured to seal this refrigerant substance in a container having thermal conductivity.

As the refrigerant substance, a refrigerant substance containing a colorant such that the presence thereof is easily visually recognized from the outside of the refrigerant pack is known, and for example, a refrigerant pack in which a refrigerant substance colored by a dye is enclosed and the enclosed amount is easily visually recognized from the outside is disclosed (refer to PTL 1).

However, in the refrigerant pack described in PTL 1, there are problems in which, even in a case where the refrigerant substance contains a dye, it is difficult to visually confirm the cooling state such as the presence/absence of freezing, and it is difficult to visually recognize whether the refrigerant pack is sufficiently cooled to the desired temperature at which cooling is possible or not, or the cooling state.

CITATION LIST

Patent Literature

[PTL 1] Japanese Unexamined Patent Application, First Publication No. 2006-97984

SUMMARY OF INVENTION

Technical Problem

An object of the present invention is to provide a refrigerant pack in which it can be easily visually recognized whether the cooling state is in an intended state or not.

Solution to Problem

The present invention provides a refrigerant pack which is provided with a refrigerant substance containing water, a precipitating component, a non-precipitating component, and a pH indicator and in which the precipitating component precipitates when the refrigerant substance freezes and is a component not corresponding to the pH indicator, the non-precipitating component does not precipitate when the refrigerant substance freezes and is a component not corresponding to the pH indicator, a change or the presence/absence of coloring in the pH indicator is reflected before and after freezing, and the refrigerant substance changes in color.

In the refrigerant pack of the present invention, the precipitating component may be an inorganic salt, and the non-precipitating component may be a thickener.

In the refrigerant substance in the refrigerant pack of the present invention, a* or b* in the L*a*b* color system before and after freezing may change from a positive value to a negative value or from a negative value to a positive value, or the difference obtained by subtracting a* before freezing from a* after freezing may become 10 or greater.

In the refrigerant substance in the refrigerant pack of the present invention, the content of the precipitating component may be 0.1% to 12% by mass, the content of the non-precipitating component may be 0.1% to 10% by mass, and the content of the pH indicator may be 1 to 30 ppm.

In the refrigerant pack of the present invention, the precipitating component may be one or more types selected from the group consisting of hydrochlorides, sulfates, nitrates, carbonates, hydrogenphosphates, hydrogencarbonates, phosphates, chlorides of alkali metals, and chlorides of alkali earth metals.

In the refrigerant pack of the present invention, the non-precipitating component may be one or more types selected from the group consisting of an acryl-based polymer, carboxyalkyl cellulose, xanthan gum, guar gum, and hydroxyalkyl guar gum.

Advantageous Effects of Invention

In a refrigerant pack of the present invention, it can be easily visually recognized whether the cooling state is in an intended state or not.

DESCRIPTION OF EMBODIMENTS

Preferable examples of the refrigerant pack of the present invention will be described below. Here, the present invention is not limited to these examples, and, for example, within a range not departing from the spirit of the present invention, addition, omission, substitution, and other modifications (amount, number, position, size, and the like) can be made.

The refrigerant pack according to the present invention is provided with a refrigerant substance containing water, a precipitating component, a non-precipitating component, and a pH indicator and in which the precipitating component precipitates when the refrigerant substance freezes and is a component not corresponding to the pH indicator, the non-precipitating component does not precipitate when the refrigerant substance freezes and is a component not corresponding to the pH indicator, a change or the presence/absence of coloring in the pH indicator is reflected before and after freezing, and the refrigerant substance changes in color.

Since, in the refrigerant pack, the color of the refrigerant substance on which the presence/absence of coloring of a pH indicator is reflected significantly changes before and after freezing, it can be easily visually recognized whether the cooling state is in an intended state (state in which an object can be sufficiently cooled) or not. In addition, the color of the refrigerant substance before and after freezing does not mainly reflect the color of the containing component itself other than the pH indicator of the precipitating component and the non-precipitating component.

The refrigerant substance significantly increases the color change depending on the change or presence/absence of coloring in the pH indicator by combining components which can adjust the acidity of the refrigerant substance as the precipitating component and the non-precipitating component and by combining the pH indicator having a suitable color change range with the precipitating component and non-precipitating component.

Hereinafter, each component will be described.

The precipitating component functions as a component of a cold insulator, and depending mainly on the type and amount thereof, the freezing temperature of the refrigerant substance is determined.

In addition, the precipitating component does not correspond to the pH indicator, is a component precipitating in a crystalline or amorphous state when the refrigerant substance is frozen, and is involved in the color change of the refrigerant substance by precipitation.

The precipitating component may be used alone or in combination of two or more types thereof.

In the precipitating component in the refrigerant substance preferably at 0° C. or higher before freezing, the dissolved amount is preferably larger, and the dissolved amount in the total amount of the precipitating component is preferably 90% by mass or greater, more preferably 95% by mass or greater, still more preferably 98% by mass or greater, and particularly preferably 100% by mass (total amount).

In addition, in the precipitating component in the refrigerant substance after freezing, the precipitated amount is preferably larger, and the precipitated amount in the total amount of the precipitating component is preferably 90% by mass or greater, more preferably 95% by mass or greater, still more preferably 98% by mass or greater, and particularly preferably 100% by mass (total amount).

The precipitating component is preferably an inorganic salt.

Examples of the metal ion as the cation configuring the inorganic salt include alkali metal ions such as a lithium ion ($Li^+$), a sodium ion ($Na^+$), and a potassium ion ($K^+$); alkali earth metal ions such as a magnesium ion ($Mg^{2+}$) and a calcium ion ($Ca^{2+}$); transition metal ions such as an iron ion ($Fe^{3+}$, $Fe^{2+}$) and a copper ion ($Cu^{2+}$, $Cu^+$); and metal ions of group 12 or group 13 such as a zinc ion ($Zn^{2+}$) and an aluminum ion ($Al^{3+}$).

Examples of the nonmetal ion as the cation configuring the inorganic salt include an ammonium ion ($NH_4$).

Examples of the anion configuring the inorganic salt include halogen ions such as a chloride ion ($Cl^-$), a bromide ion ($Br^-$), and an iodide ion ($I^-$); a sulfate ion ($SO_4^{2-}$); a nitrate ion ($NO_3^-$); a carbonate ion ($CO_3^{2-}$); a hydrogencarbonate ion ($HCO_3^-$); a hydrogensulfate ion ($HSO_4^-$); a phosphate ion ($PO_4^{3-}$); a hydrogenphosphate ion ($HPO_4^{2-}$); a dihydrogenphosphate ion ($H_2PO_4^-$); a sulfite ion ($SO_3^{2-}$); a thiosulfate ion ($S_2O_3^{2-}$); a chlorate ion ($ClO_3^-$); a perchlorate ion ($ClO_4^-$); and an ion having a group obtained by removing a hydrogen ion (H+) from the acid group such as a carboxy group (—C(=O)—OH) or a sulfo group (—S(=O)$_2$—OH).

Although the inorganic salt is not particularly limited, examples thereof include alkali metal chlorides such as sodium chloride (NaCl) and potassium chloride (KCl); hydrochlorides such as ammonium chloride ($NH_4Cl$); sulfates such as sodium sulfate ($Na_2SO_4$), potassium sulfate ($K_2SO_4$), ammonium sulphate (($NH_4)_2SO_4$), magnesium sulfate ($MgSO_4$), aluminum sulfate ($Al_2(SO_4)_3$), nickel sulfate ($NiSO_4$), aluminum potassium sulfate ($AlK(SO_4)_2$), and ammonium alum ($Al(NH_4)(SO_4)_2$); nitrates such as sodium nitrate ($NaNO_3$), potassium nitrate ($KNO_3$), ammonium nitrate ($NH_4NO_3$), calcium nitrate tetrahydrate ($Ca(NO_3)_2 \cdot 4H_2O$), and calcium nitrate ($Ca(NO_3)_2$); carbonates such as potassium carbonate ($K_2CO_3$); hydrogencarbonates such as potassium hydrogen carbonate ($KHCO_3$) and sodium hydrogen carbonate ($NaHCO_3$); chlorides of alkali earth metals such as calcium chloride ($CaCl_2$) and magnesium chloride ($MgCl_2$); hydrogenphosphates such as sodium dihydrogen phosphate ($NaH_2PO_4$), disodium hydrogen phosphate ($Na_2HPO_4$), potassium dihydrogen phosphate ($KH_2PO_4$), dipotassium hydrogen phosphate ($K_2HPO_4$), ammonium dihydrogen phosphate ($NH_4H_2PO_4$), and diammonium hydrogen phosphate (($NH_4)_2HPO_4$); phosphates such as trisodium phosphate ($Na_3PO_4$); sulfites such as sodium sulfite ($Na_2SO_3$); chlorates such as potassium chlorate ($KClO_3$); perchlorates such as sodium perchlorate ($NaClO_4$); thiosulfates such as sodium thiosulfate ($Na_2S_2O_3$); bromides of alkali metals such as potassium bromide (KBr) and sodium bromide (NaBr); iodides of alkali metals such as potassium iodide (KI) and sodium iodide (NaI); and borates such as borax ($Na_2B_4O_7$). The inorganic salt may be used alone or in combination of two or more types thereof.

The inorganic salt is preferably one or more types selected from the group consisting of hydrochlorides, sulfates, nitrates, carbonates, hydrogenphosphates, hydrogencarbonates, phosphates, chlorides of alkali metals, chlorides of alkali earth metal, sulfites, chlorates, perchlorates, thiosulfates, bromides of alkali metals, iodides of alkali metals, and borates.

In addition, the inorganic salt is more preferably one or more types selected from the group consisting of hydrochlorides, sulfates, nitrates, carbonates, hydrogenphosphates, hydrogencarbonates, phosphates, chlorides of alkali metals, and chlorides of alkali earth metal.

By using such an inorganic salt, the refrigerant substance changes significantly in color before and after freezing, and is excellent in handling properties.

The content of the precipitating component in the refrigerant substance is preferably an amount in which a pH (A) described below is within a predetermined range, preferably 0.1% to 12% by mass, more preferably 0.1% to 10% by mass, and may be 0.5% to 5% by mass.

The non-precipitating component does not precipitate when the refrigerant substance freezes, and is a component not corresponding to the pH indicator. "The non-precipitating component does not precipitate when the refrigerant substance freezes" in the present specification means that when the refrigerant substance freezes, the non-precipitating component is solidified in a state of being dissolved in water, and it is estimated that the state is one in which the non-precipitating component is solidified while surrounded by water molecules without aggregation of the molecules of the non-precipitating component in a large amount, and the state is not one in which the non-precipitating component is solidified by aggregation of the molecules of the non-precipitating component in a large amount.

The non-precipitating component may be used alone or in combination of two or more types thereof.

In the non-precipitating component in the refrigerant substance before and after freezing, the precipitated amount is preferably smaller, and the precipitated amount in the total amount of the non-precipitating component is preferably 10% by mass or less, more preferably 5% by mass or less, still more preferably 2% by mass or less, and particularly preferably 0% by mass (total amount is not precipitated).

The non-precipitating component is preferably a thickener or a surfactant, and more preferably a thickener.

Although the thickener is not particularly limited, examples thereof include acryl-based polymers (compound having a polyacrylic acid skeleton) such as polyacrylic acid and sodium polyacrylate; carboxyalkyl celluloses such as carboxymethyl cellulose (CMC); guar gum; hydroxyalkyl guar gums such as hydroxypropyl guar gum; pectin; xanthan gum; tamarind gum; carrageenan; and alkylene glycols such as propylene glycol.

The thickener may be used alone or in combination of two or more types thereof.

The thickener is preferably one or more types selected from the group consisting of an acryl-based polymer, carboxyalkyl cellulose, xanthan gum, guar gum, hydroxyalkyl guar gum, pectin, tamarind gum, carrageenan, and alkylene glycol.

In addition, the thickener is more preferably one or more types selected from the group consisting of an acryl-based polymer, carboxyalkyl cellulose, xanthan gum, guar gum, and hydroxyalkyl guar gum.

By using such a thickener, the refrigerant substance changes significantly in color before and after freezing, and is excellent in handling properties.

Although the surfactant is not particularly limited, examples thereof include alkyl sulfates such as sodium dodecyl sulfate; alkyl carboxylates such as sodium decanoate; N-alkyl acrylamides such as N-isopropyl acrylamide; polyoxyethylene dialkyl ethers such as polyoxyethylene octyl dodecyl ether; polyoxyethylene monoalkyl ethers such as polyoxyethylene lauryl ether; and polyoxyethylene monoalkenyl ethers such as polyoxyethylene oleyl ether.

The surfactant may be used alone or in combination of two or more types thereof.

The content of the non-precipitating component in the refrigerant substance is preferably an amount in which a pH (B) described below is within a predetermined range, preferably 0.1% to 10% by mass, and more preferably 0.3% to 4% by mass.

In the refrigerant substance, the precipitating component is an inorganic salt, and the non-precipitating component is preferably a thickener. Such a refrigerant substance changes significantly in color before and after freezing, and is excellent in handling properties.

The pH indicator (acid base indicator) determines the color of the refrigerant substance by reflecting the presence/absence of coloring. By containing a pH indicator, the refrigerant substance changes in color before and after freezing.

As the pH indicator, a known pH indicator may be used, and is not particularly limited.

The pH indicator has a pH range in which the change in color is observed, that is, a color change range. The pH indicator is present in a state of being divided into a dissociation form and a non-dissociation form in a solution, the dissociation equilibrium is formed therebetween, and the colors that the dissociation form and the non-dissociated exhibit are different, but out of the color change range, the equilibrium is significantly biased to either of the dissociation form or the non-dissociation form, and the color of only one side is seen. In the pH indicator in the color change range, a dissociation form and an undissociation form are mixed in an amount to the extent capable of being compared, and a mixed color of the colors of both sides is seen ("Chemical Encyclopedia Compact Edition, 39th printing, Sep. 15, 2006, Kyoritsu Shuppan Co., Ltd.").

The color change range (pH) of the pH indicator in the present invention is preferably within a range of 2.8 to 11.0. The main pH indicators are shown in Table 1. In Table 1, together with the pH indicators, the color change range and the color changes thereof are described. "Color change (low pH→high pH)" in Table 1 shows a color change which a pH indicator shows in the color change range when the pH of the liquid containing the pH indicator changes from a specific value to a value higher than the specific value, and for example, "red→yellow" shows that, in the course in which the pH of the liquid becomes high, the pH indicator changes the color of the liquid from red to yellow.

TABLE 1

| pH indicator | Color change range (pH) | Color change (low pH → high pH) |
| --- | --- | --- |
| Methyl yellow | 2.9 to 4.0 | Red → yellow |
| Bromophenol blue (BPB) | 3.0 to 4.6 | Yellow → violet |
| Congo red | 3.0 to 5.0 | Violet → red |
| Methyl orange (MO) | 3.1 to 4.4 | Red → orange |
| Bromocresol green (BCG) | 4.0 to 5.6 | Yellow → blue |
| Methyl red (MR) | 4.2 to 6.2 | Red → yellow |
| Litmus | 4.5 to 8.3 | Red → blue |
| Methyl purple | 4.8 to 5.4 | Violet → green |
| p-Nitrophenol | 5.0 to 7.0 | No color → yellow |
| Bromocresol purple (BCP) | 5.2 to 6.8 | Yellow → violet |
| Chlorophenol red | 5.4 to 6.8 | Yellow → red |
| Bromothymol blue (BTB) | 6.0 to 7.6 | Yellow → blue |
| Neutral red | 6.8 to 8.0 | Red → yellow |
| Phenol red (PR) | 6.8 to 8.4 | Yellow → red |
| p-Naphtholphthalein | 7.1 to 8.7 | Yellow → blue |
| Cresol red | 7.2 to 8.8 | Yellow → red |
| Phenol phthalein (PP) | 7.8 to 10.0 | No color → red violet |
| Thymol blue | 8.0 to 9.6 | Yellow → blue |
| Thymol phthalein | 9.3 to 10.5 | No color → blue |

The pH indicator may be used alone or in combination of two or more types thereof, but typically, is preferably used alone.

The content of the pH indicator in the refrigerant substance is not particularly limited as long as the intended color change in the refrigerant substance is achieved, and the content is preferably 1 to 30 ppm, and more preferably 5 to 20 ppm.

In addition to water, the precipitating component, the non-precipitating component, and the pH indicator, the refrigerant substance may contain other components which do not correspond thereto within a range not impairing the effects of the present invention. As other components, various additives such as solvents other than water and a preservative can be exemplified.

The solvent is preferably a solvent capable of dissolving the precipitating component, the non-precipitating component, and the pH indicator, and as such a solvent, alcohol can be exemplified.

The solvent may be used alone or in combination of two or more types thereof.

Water and the solvent function as a component of a cold insulator, and together with the precipitating component, depending mainly on the types and amounts thereof, the freezing temperature of the refrigerant substance is determined.

In the refrigerant substance, the ratio of the content of the solvent with respect to the total content of water and the solvent is preferably 10% by mass or less, more preferably 5% by mass or less, and particularly preferably 2% by mass or less.

As the preservative, a food preservative and an antioxidant can be exemplified, and sodium pyrithione, paraben (paraoxybenzoate), protamine, and an organic nitrogen sulfur-based compound can be exemplified.

In the refrigerant substance, the ratio of the total content of the precipitating component, the non-precipitating component, and the pH indicator with respect to the total content of the components (components other than the precipitating component, the non-precipitating component, the pH indicator, and the solvent) other than water and the solvent is preferably 90% by mass or greater, more preferably 95% by mass or greater, and may be 100% by mass. If the ratio of the total content is the above lower limit value or greater, the refrigerant substance changes more significantly in color before and after freezing.

In the refrigerant substance, it is particularly preferable that the content of the precipitating component be 0.1% to 10% by mass, the content of the non-precipitating component be 0.1% to 10% by mass, and the content of the pH indicator be 1 to 30 ppm. Such a refrigerant substance changes significantly in color before and after freezing, and is excellent in handling properties.

As a preferable refrigerant substance, a refrigerant substance which satisfies one or more of the following conditions (i) to (iii) can be exemplified.

(i) Before and after freezing, a* in the L*a*b* color system changes from a positive value to a negative value or from a negative value to a positive value. That is, in a case where a* of the refrigerant substance after freezing is defined as a1* and a* of the refrigerant substance before freezing is defined as a2*, a relationship of a1*<0<a2*, or a2*<0<a1* is satisfied.

(ii) Before and after freezing, b* in the L*a*b* color system changes from a positive value to a negative value or from a negative value to a positive value. That is, in a case where b* of the refrigerant substance after freezing is defined as b1* and b* of the refrigerant substance before freezing is defined as b2*, a relationship of b1*<0<b2*, or b2*<0<b1* is satisfied.

(iii) The difference obtained by subtracting a* before freezing from a* after freezing becomes 10 or greater (+10 or greater). That is, in a case where a* of the refrigerant substance after freezing is defined as a1* and a* of the refrigerant substance before freezing is defined as a2*, a relationship of a1*−a2*≥10 is satisfied.

Here, a1* and b1* are the values of the same period, and a2* and b2* are the values of the same period.

The refrigerant substance satisfies one or more (one, two, or all) relationships of (i), (ii), and (iii), and changes more significantly in color before and after freezing.

As a preferable refrigerant substance, a refrigerant substance which satisfies one or more of the following conditions (iv) and (v) can also be exemplified.

(iv) the pH (hereinafter, referred to as "pH (A)") in the case of replacing all contained components (the non-precipitating component, the pH indicators, and other components) other than the precipitating component and water with the same mass of water becomes 7.0 to 11.5, the pH (hereinafter, referred to as "pH (B)") in the case of replacing all contained components (the precipitating component, the pH indicators, and other components) other than the non-precipitating component and water with the same mass of water becomes 2.7 to 9.0, and pH (A) and pH (B) show values in the pH ranges different from each other among three pH ranges of a pH range lower than the color change range of the pH indicator, a pH range in the color change range, and a pH range higher than the color change range.

(v) the pH (hereinafter, referred to as "pH (α)") in the case of replacing all contained components (the non-precipitating component, the pH indicators, and other components) other than the precipitating component and water with the same mass of water becomes 4.5 or higher and lower than 7.0, the pH (hereinafter, referred to as "pH (β)") in the case of replacing all contained components (the precipitating component, the pH indicators, and other components) other than the non-precipitating component and water with the same mass of water becomes 5.5 to 10.3, and pH (α) and pH (β) show values in the pH ranges different from each other among three pH ranges of a pH range lower than the color change range of the pH indicator, a pH range in the color change range, and a pH range higher than the color change range.

Here, "pH (A) and pH (B) show values in the pH ranges different from each other among three pH ranges of a pH range lower than the color change range of the pH indicator, a pH range in the color change range, and a pH range higher than the color change range", for example, means that in a case where pH (A) shows a value in a pH range lower than the color change range of the pH indicator, pH (B) shows a pH value in the color change range of the pH indicator, or a pH value higher than the color change range of the pH indicator.

In addition, pH (A) and pH (B) are preferably pHs at a temperature at which the pH indicator is dissolved in the refrigerant substance.

pH (A) corresponds to the pH of the precipitating component-containing water (for example, precipitating component aqueous solution) containing only the precipitating component in the same content (% by mass) as the content (% by mass) in the refrigerant substance. pH (A) is preferably 11.2 or less, and more preferably 10.8 or less. In addition, pH (A) is preferably 7.2 or greater, and more preferably 7.4 or greater.

pH (B) corresponds to the pH of the non-precipitating component-containing water (for example, non-precipitating component aqueous solution) containing only the non-precipitating component in the same content (% by mass) as the content (% by mass) in the refrigerant substance. pH (B) is preferably 8.8 or less, and more preferably 8.4 or less. In addition, pH (B) is preferably 2.5 or greater, and more preferably 2.7 or greater.

pH (α) and pH (A) have the same meaning. pH (α) is preferably 6.9 or less, and more preferably 6.7 or less. In addition, pH (α) is preferably 4.7 or greater, and more preferably 4.9 or greater.

pH (β) and pH (B) have the same meaning. pH (β) is preferably 5.7 or greater, and more preferably 5.9 or greater.

As a preferable refrigerant substance, furthermore, a refrigerant substance which satisfies one or more of the following conditions (vi) and (vii) can also be exemplified.

(vi) The pH (pH (A)) in the case of replacing all contained components (the non-precipitating component, the pH indicators, and other components) other than the precipitating component and water with the same mass of water becomes 7.0 to 11.5, the pH (pH (B)) in the case of replacing all contained components (the precipitating component, the pH indicators, and other components) other than the non-precipitating component and water with the same mass of water becomes 2.7 to 9.0, and pH (hereinafter, referred to as "pH (C)" in some cases) of the refrigerant substance before freezing and pH (B) show values in the pH ranges different from each other among three pH ranges of a pH range lower than the color change range of the pH indicator, a pH range in the color change range, and a pH range higher than the color change range.

(vii) The pH (pH (α)) in the case of replacing all contained components (the non-precipitating component, the pH indicators, and other components) other than the precipitating component and water with the same mass of water becomes 4.5 or higher and lower than 7.0, the pH (pH (β)) in the case of replacing all contained components (the precipitating component, the pH indicators, and other components) other than the non-precipitating component and water with the same mass of water becomes 5.5 to 10.3, and pH (pH (C)) of the refrigerant substance before freezing and pH (β) show values in the pH ranges different from each other among three pH ranges of a pH range lower than the color change range of the pH indicator, a pH range in the color change range, and a pH range higher than the color change range.

pH (C) is preferably a pH at a temperature at which the pH indicator is dissolved in the refrigerant substance.

The refrigerant substance satisfies one or more (one or two) conditions of (iv) and (v), or satisfies one or more (one or two) conditions of (vi) and (vii), and changes more significantly in color before and after freezing.

The refrigerant substance which satisfies the condition of (iv) or (v), or (vi) or (vii) significantly increases the color change depending on the change or presence/absence of coloring in the pH indicator, by combining components of which the pH of the aqueous solution of a predetermined concentration is within a specific range as the precipitating component and the non-precipitating component affecting coloring of the pH indicator and by combining the pH indicator having a suitable color change range with this precipitating component and this non-precipitating component.

In the refrigerant substance, the color difference (ΔE) before and after freezing is preferably 8 or greater, more preferably 10 or greater, and still more preferably 11 or greater.

In addition, although the upper limit value of the color difference (ΔE) before and after freezing of the refrigerant substance is not particularly limited, for example, the upper limit value may be 50, may be 48, and may be 46.

It is estimated that in the refrigerant substance, while, in the stage before freezing, any of protonation and deprotonation in the pH indicator is affected by the precipitating component dissolved in the refrigerant substance, in the stage after freezing, by most or all of the precipitating components being precipitated in the refrigerant substance, any of protonation and deprotonation in the pH indicator is not affected by the precipitating component at all or is affected weakly. Thus, it is estimated that a change or presence/absence of coloring in the pH indicator is reflected, and before and after freezing, the refrigerant substance changes significantly in color.

The refrigerant substance can be obtained by blending water, the precipitating component, the non-precipitating component, the pH indicator, and, if necessary, other components.

The blending method of the respective components is not particularly limited, and at a temperature higher than the freezing temperature of the refrigerant substance, it is possible to arbitrarily adjust such that respective components are uniformly dissolved or dispersed.

For example, at the time of blending respective components, mixing may be performed after all of the components are added, mixing may be performed while sequentially adding some of the components, or mixing may be performed while sequentially adding all of the components.

The mixing method is not particularly limited, and may be suitably selected from known methods such as a method of mixing by rotating a stirrer, a stirring blade, or the like; a method of mixing using a mixer, a three-roll mill, a kneader, a bead mill, or the like; and a method of mixing by applying ultrasound.

The refrigerant pack according to the present invention is provided with the refrigerant substance, and for example, is configured to hold the refrigerant substance by holding means such as a container capable of enclosing a liquid material.

The material of the holding means is not particularly limited as long as it has transparency to the extent in which the color change of the held refrigerant substance can be visually recognized, and preferable examples include polyolefins such as polyethylene and polypropylene; polyamide; and synthetic resins such as polyester. Among these, from the viewpoint of excellent low-temperature antibrittleness, water resistance, and chemical resistance, polyolefins are preferable, and high density polyethylene which is easily molded and has a high strength is more preferable.

Since the refrigerant substance changes significantly in color before and after freezing, the presence/absence of freezing can be easily visually recognized. The color change of the refrigerant substance can be visually recognized from the outside of the refrigerant pack, and as a result, it can be easily visually recognized whether the refrigerant pack is sufficiently cooled to the desired temperature or not.

In addition, since even in a case where repeatedly cooling and raising the temperature such as freezing and thawing, the effects of the refrigerant substance are not impaired, the refrigerant pack provided with the same is suitable also for repeated use.

EXAMPLES

Hereinafter, the present invention will be described in more detail based on specific examples. However, the present invention is not limited to the examples described below. Hereinafter, the unit "ppm" of the content (blending amount, concentration) of the pH indicator is based on mass ratio.

The raw materials used in the examples and the comparative examples are shown below.

(Thickening Agent)
Acryl-based polymer (1): "ARONVIS AH-305X" manufactured by Toagosei Chemical Industry Co., Ltd.
Acryl-based polymer (2): "AQUPEC HV-505ED" manufactured by Sumitomo Seika Chemicals Co., Ltd.
Acryl-based polymer (3): "AQUALIC AS58" manufactured by NIPPON SHOKUBAI CO., LTD.
Acryl-based polymer (4): "AQUALIC FH-S" manufactured by NIPPON SHOKUBAI CO., LTD.
Acryl-based polymer (5): "AQUALIC IH-G" manufactured by NIPPON SHOKUBAI CO., LTD.
Acryl-based polymer (6): "JUNLON PW121" manufactured by Toagosei Chemical Industry Co., Ltd.
CMC: carboxymethyl cellulose (manufactured by Kanto Chemical Co., Inc.)
XTG: xanthan gum (manufactured by SANSHO Co., Ltd.) (pH Indicator)
BTB: bromothymol blue (manufactured by Wako Pure Chemical Industries, Ltd.)
BCP: bromocresol purple (manufactured by Wako Pure Chemical Industries, Ltd.)
PR: phenol red (manufactured by Wako Pure Chemical Industries, Ltd.)
TP: thymolphthalein (manufactured by Wako Pure Chemical Industries, Ltd.)
BPB: bromophenol blue (manufactured by Wako Pure Chemical Industries, Ltd.)

Example 1

<Production of Refrigerant Substance and Refrigerant Pack>

At room temperature (20° C. to 25° C.), water (96.7 parts by mass), BTB, an acryl-based polymer (1) (1.3 parts by mass), and dipotassium hydrogen phosphate (2 parts by mass) were added, followed by mixing, whereby a refrigerant substance was obtained. At this time, the blending amount of BTB was adjusted such that the content in the obtained refrigerant substance became 10 ppm. Each blending component and concentration other than water, pH (A), and pH (B) are shown in Table 2. Here, pH (A) has the same meaning as pH ($\alpha$), and pH (B) has the same meaning as pH ($\beta$). Then, pH (C) of the obtained refrigerant substance was measured. The results are shown in Table 6. All of pH (A), pH (B), and pH (C) were measured at a temperature of the measurement object of 25° C.

In Table 2, the concentration described in a "% by mass" unit in the column of pH (A) shows the concentration of the inorganic salt aqueous solution at the time of measuring pH (A). In the same manner, the concentration described in a "% by mass" unit in the column of pH (B) shows the concentration of the thickener aqueous solution at the time of measuring pH (B). In addition, "color change" described in the column of the color change range of the pH indicator shows a color change which the pH indicator shows in the color change range when the pH of the liquid containing the pH indicator changes from a specific value to a value higher than the specific value, and for example, "yellow→blue" shows that, in the course in which the pH of the liquid becomes high, the pH indicator changes the color of the liquid from yellow to blue.

Next, the obtained refrigerant substance was sealed in a container made of high density polyethylene, whereby a refrigerant pack was obtained.

<Evaluation of Refrigerant Substance>

(Color Difference ($\Delta E$))

The obtained refrigerant substance (refrigerant pack) was cooled to −25° C. During this time, the refrigerant substance was frozen at a temperature higher than −25° C., and changed in color before and after freezing. Then, L*, a*, and b* of the refrigerant substance before freezing and the refrigerant substance after freezing were measured using a color difference measuring instrument ("X-rite 530" manufactured by X-Rite Inc.) under the following conditions.

(Measurement Conditions)

For the refrigerant substance sealed in a container made of high-density polyethylene, the values of L*, a*, and b* before freezing were measured using a color difference measuring instrument from the top of the container. Furthermore, the refrigerant substance was frozen in a freezing chamber at −25° C., and the values of L*, a*, and b* immediately after freezing were measured in the same manner as in the case of before freezing.

In addition, from the obtained measurement values of L*, a*, and b*, according to the following Equation (I), the color difference ($\Delta E$) of the refrigerant substance before and after freezing was calculated. The results are shown in Table 4.

(Calculation of (Color Difference ($\Delta E$))

$$\Delta E = [(L1^* - L2^*)^2 + (a1^* - a2^*)^2 + (b1^* - b2^*)^2]^{1/2} \quad (I)$$

(In the equation, L1* is a value of L* of the refrigerant substance after freezing, L2* is a value of L* of the refrigerant substance before freezing, a1* is a value of a* of the refrigerant substance after freezing, a2* is a value of a* of the refrigerant substance after freezing, b1* is a value of b* of the refrigerant substance after freezing, b2* is a value of b* of the refrigerant substance before freezing, L1*, a1*, and b1* are values of the same period, and L2*, a2*, and b2* are values of the same period.)

(Color Change)

At the time of the above $\Delta E$ calculation, the color change of the refrigerant substance before and after freezing was visually evaluated according to the following criteria. The results are shown in Table 4.

In Table 4, "color change" described in the column of the evaluation result shows the color change of the refrigerant substance before and after freezing, and for example, "green→yellow" shows that the color of the refrigerant substance is green before freezing and is yellow after freezing.

A: color change before and after freezing was significant, and the cooling state was extremely easily visually recognized.

B: color change before and after freezing was discriminable, and the cooling state could be visually recognized.

C: color change before and after freezing was unclear, and the cooling state was difficult to be visually recognized or could not be visually recognized.

<Production of Refrigerant Substance and Refrigerant Pack, and Evaluation of Refrigerant Substance>

Examples 2 to 7 and Comparative Examples 1 to 4

Refrigerant substances and refrigerant packs were produced in the same manner as Example 1 except that the blending components and the concentrations of the refrigerant substance were set as shown in Table 2, and the refrigerant substance was evaluated. The results are shown in Table 4. In addition, pH (C) of the refrigerant substance is shown in Table 6.

Examples 8 to 17 and Comparative Examples 5 to 10

Refrigerant substances and refrigerant packs were produced in the same manner as Example 1 except that the blending components and the concentrations of the refrigerant substance were set as shown in Table 3, and the refrigerant substance was evaluated. Evaluation of the refrigerant substance was performed only for the color change by visual observation. The results are shown in Table 5. In addition, pH (C) of the refrigerant substance is shown in Table 6.

In all of the refrigerant substances of Examples 1 to 17 and Comparative Examples 1 to 10, the inorganic salt was completely dissolved before freezing, but the total amount or almost total amount of the inorganic salt was precipitated after freezing.

In addition, in all of Examples 1 to 17 and Comparative Examples 1 to 10, the content of the pH indicator of the refrigerant substance was 10 ppm.

TABLE 2

| | Blending component | | | | | |
|---|---|---|---|---|---|---|
| | Inorganic salt | | Thickener | | pH indicator | |
| | Name | pH (A) (% by mass) | Name | pH (B) (% by mass) | Name | Color change range (color change) |
| Example 1 | Dipotassium hydrogen phosphate | 8.9 (2.0) | Acryl-based polymer (1) | 5.2 (1.3) | BTB | 6.0 to 7.6 (yellow → blue) |
| Example 2 | Dipotassium hydrogen phosphate | 8.9 (2.0) | Acryl-based polymer (1) | 5.16 (1.3) | BCP | 5.2 to 6.8 (yellow → violet) |
| Example 3 | Dipotassium hydrogen phosphate | 8.9 (2.0) | Acryl-based polymer (1) | 5.2 (1.3) | PR | 6.8 to 8.4 (yellow → red) |
| Example 4 | Dipotassium hydrogen phosphate | 8.9 (2.0) | CMC | 6.2 (1.3) | BTB | 6.0 to 7.6 (yellow → blue) |
| Example 5 | Dipotassium hydrogen phosphate | 8.9 (2.0) | XTG | 5.4 (1.3) | BTB | 6.0 to 7.6 (yellow → blue) |
| Example 6 | Diammonium hydrogen phosphate | 7.9 (2.0) | Acryl-based polymer (2) | 2.9 (1.0) | BCP | 5.2 to 6.8 (yellow → violet) |
| Example 7 | Sodium sulfate | 6.3 (2.0) | CMC | 6.2 (1.3) | BTB | 6.0 to 7.6 (yellow → blue) |
| Comparative Example 1 | Potassium carbonate | 11.6 (2.0) | Acryl-based polymer (1) | 5.2 (1.3) | BTB | 6.0 to 7.6 (yellow → blue) |
| Comparative Example 2 | Dipotassium hydrogen phosphate | 8.9 (2.0) | Acryl-based polymer (1) | 5.2 (1.3) | TP | 9.3 to 10.5 (no color → blue) |
| Comparative Example 3 | Dipotassium hydrogen phosphate | 8.9 (2.0) | Acryl-based polymer (1) | 5.2 (1.3) | BPB | 3.0 to 4.6 (yellow → violet) |
| Comparative Example 4 | Dipotassium hydrogen phosphate | 8.9 (2.0) | Acryl-based polymer (3) | 2.6 (1.3) | BTB | 6.0 to 7.6 (yellow → blue) |

TABLE 3

| | Blending component | | | | | |
|---|---|---|---|---|---|---|
| | Inorganic salt | | Thickener | | pH indicator | |
| | Name | pH (A) (% by mass) | Name | pH (B) (% by mass) | Name | Color change range (color change) |
| Example 8 | Disodium hydrogen phosphate | 9.2 (2.0) | Acryl-based polymer (1) | 5.2 (1.3) | BTB | 6.0 to 7.6 (yellow → blue) |
| Example 9 | Diammonium hydrogen phosphate | 7.9 (2.0) | Acryl-based polymer (1) | 5.2 (1.3) | BTB | 6.0 to 7.6 (yellow → blue) |
| Example 10 | Diammonium hydrogen phosphate | 7.9 (2.0) | Acryl-based polymer (1) | 5.2 (1.3) | BCP | 5.2 to 6.8 (yellow → violet) |
| Example 11 | Diammonium hydrogen phosphate | 7.9 (2.0) | CMC | 6.2 (1.3) | BTB | 6.0 to 7.6 (yellow → blue) |
| Example 12 | Sodium sulfate | 6.3 (2.0) | Acryl-based polymer (4) | 9.2 (1.3) | BTB | 6.0 to 7.6 (yellow → blue) |
| Example 13 | Sodium sulfate | 6.3 (2.0) | Acryl-based polymer (5) | 10.2 (1.3) | BTB | 6.0 to 7.6 (yellow → blue) |
| Example 14 | Calcium nitrate tetrahydrate | 5.7 (2.0) | CMC | 6.2 (1.3) | BTB | 6.0 to 7.6 (yellow → blue) |
| Example 15 | Ammonium chloride | 5.5 (2.0) | CMC | 6.2 (1.3) | BTB | 6.0 to 7.6 (yellow → blue) |
| Example 16 | Diammonium hydrogen phosphate | 7.9 (2.0) | Acryl-based polymer (2) | 3.0 (0.8) | BCP | 5.2 to 6.8 (yellow → violet) |
| Example 17 | Diammonium hydrogen phosphate | 7.9 (2.0) | Acryl-based polymer (2) | 3.1 (0.6) | BCP | 5.2 to 6.8 (yellow → violet) |
| Comparative Example 5 | Sodium sulfate | 6.3 (2.0) | Acryl-based polymer (1) | 5.2 (1.3) | BTB | 6.0 to 7.6 (yellow → blue) |
| Comparative Example 6 | Sodium sulfate | 6.3 (2.0) | XTG | 5.4 (1.3) | BTB | 6.0 to 7.6 (yellow → blue) |
| Comparative Example 7 | Calcium nitrate tetrahydrate | 5.7 (2.0) | Acryl-based polymer (1) | 5.2 (1.3) | BTB | 6.0 to 7.6 (yellow → blue) |
| Comparative Example 8 | Dipotassium hydrogen phosphate | 8.9 (2.0) | Acryl-based polymer (5) | 10.2 (1.3) | BTB | 6.0 to 7.6 (yellow → blue) |
| Comparative Example 9 | Dipotassium hydrogen phosphate | 8.9 (2.0) | Acryl-based polymer (4) | 9.2 (1.3) | BTB | 6.0 to 7.6 (yellow → blue) |
| Comparative Example 10 | Ammonium dihydrogen phosphate | 4.4 (2.0) | CMC | 6.2 (1.3) | BTB | 6.0 to 7.6 (yellow → blue) |

TABLE 4

| | Evaluation results | | | | | | | | | |
|---|---|---|---|---|---|---|---|---|---|---|
| | Before freezing | | | After freezing | | | | | | Color |
| | L2* | a2* | b2* | L1* | a1* | b1* | a1* − a2* | b1* − b2* | ΔE | change |
| Example 1 | 47.03 | −12.54 | 9.64 | 41.50 | −2.49 | 11.30 | 10.05 | 1.66 | 11.59 | A (green → yellow) |
| Example 2 | 32.86 | 21.94 | −18.71 | 44.45 | −4.02 | 14.20 | −25.96 | 32.91 | 43.49 | A (violet → yellow) |
| Example 3 | 47.08 | 17.24 | 30.33 | 44.35 | −2.73 | 21.57 | −19.97 | −8.76 | 21.98 | A (red → yellow) |
| Example 4 | 35.88 | −3.91 | −20.48 | 53.05 | −1.97 | 12.20 | 1.94 | 32.68 | 36.97 | B (blue → green) |
| Example 5 | 33.02 | −6.56 | −6.14 | 53.12 | −5.99 | 9.65 | 0.57 | 15.79 | 25.57 | B (blue → yellow green) |
| Example 6 | 37.67 | 9.59 | −11.19 | 43.84 | −3.01 | 6.78 | −12.60 | 17.97 | 22.80 | A (violet → yellow) |
| Example 7 | 38.22 | −6.57 | −17.83 | 49.79 | −3.55 | 16.77 | 3.02 | 34.60 | 36.61 | A (green → yellow) |
| Comparative Example 1 | 34.61 | 1.88 | −28.39 | 35.12 | 2.85 | −15.63 | 0.97 | 12.76 | 12.81 | C (blue → thin blue) |
| Comparative Example 2 | 60.24 | −0.06 | −1.68 | 44.31 | −0.24 | −0.80 | −0.18 | 0.88 | 15.96 | C (no color → white) |
| Comparative Example 3 | 33.22 | 28.70 | −34.60 | 27.13 | 6.99 | −19.42 | −21.71 | 15.18 | 27.18 | C (violet → thin violet) |
| Comparative Example 4 | 55.11 | −4.97 | 26.81 | 38.94 | −0.09 | 13.70 | 4.88 | −13.11 | 21.38 | C (yellow → yellow) |

TABLE 5

| | Evaluation results | | | | | | | | | |
|---|---|---|---|---|---|---|---|---|---|---|
| | Before freezing | | | After freezing | | | | | | Color |
| | L2* | a2* | b2* | L1* | a1* | b1* | a1* − a2* | b1* − b2* | ΔE | change |
| Example 8 | — | — | — | — | — | — | — | — | — | A (green → yellow) |
| Example 9 | — | — | — | — | — | — | — | — | — | A (green → yellow) |
| Example 10 | — | — | — | — | — | — | — | — | — | A (violet → yellow) |
| Example 11 | — | — | — | — | — | — | — | — | — | B (blue → thin blue) |
| Example 12 | — | — | — | — | — | — | — | — | — | A (blue → green) |
| Example 13 | — | — | — | — | — | — | — | — | — | B (blue → thin blue) |
| Example 14 | — | — | — | — | — | — | — | — | — | A (green → yellow) |
| Example 15 | — | — | — | — | — | — | — | — | — | B (yellow green → white) |

TABLE 5-continued

| | Evaluation results | | | | | | | | Color change |
|---|---|---|---|---|---|---|---|---|---|
| | Before freezing | | | After freezing | | | | | |
| | L2* | a2* | b2* | L1* | a1* | b1* | a1* − a2* | b1* − b2* | ΔE | |
| Example 16 | — | — | — | — | — | — | — | — | — | A (violet → yellow) |
| Example 17 | — | — | — | — | — | — | — | — | — | A (violet → yellow) |
| Comparative Example 5 | — | — | — | — | — | — | — | — | — | C (yellow → yellow) |
| Comparative Example 6 | — | — | — | — | — | — | — | — | — | C (yellow → yellow) |
| Comparative Example 7 | — | — | — | — | — | — | — | — | — | C (yellow → yellow) |
| Comparative Example 8 | — | — | — | — | — | — | — | — | — | C (blue → blue) |
| Comparative Example 9 | — | — | — | — | — | — | — | — | — | C (blue → blue) |
| Comparative Example 10 | — | — | — | — | — | — | — | — | — | C (yellow → yellow) |

TABLE 6

| | pH (C) |
|---|---|
| Example 1 | 6.6 |
| Example 2 | 6.6 |
| Example 3 | 6.6 |
| Example 4 | 8.9 |
| Example 5 | 8.3 |
| Example 6 | 6.2 |
| Example 7 | 5.8 |
| Example 8 | 6.7 |
| Example 9 | 6.5 |
| Example 10 | 6.5 |
| Example 11 | 8.8 |
| Example 12 | 7.8 |
| Example 13 | 8.2 |
| Example 14 | 5.6 |
| Example 15 | 5.4 |
| Example 16 | 6.3 |
| Example 17 | 6.5 |
| Comparative Example 1 | 10.5 |
| Comparative Example 2 | 6.6 |
| Comparative Example 3 | 6.6 |
| Comparative Example 4 | 5.6 |
| Comparative Example 5 | 4.5 |
| Comparative Example 6 | 4.6 |
| Comparative Example 7 | 4.3 |
| Comparative Example 8 | 9.0 |
| Comparative Example 9 | 8.8 |
| Comparative Example 10 | 4.9 |

As is apparent from the above results, in Examples 1 to 17, with the precipitation of the inorganic salt at the time of freezing, the change in coloring of the pH indicator was reflected, and thus, the color of the refrigerant substance changed clearly, and the cooling state could be easily visually recognized In contrast, in Comparative Examples 1 to 10, even inorganic salt was precipitated at the time of freezing, the color change of the refrigerant substance was unclear, and the cooling state was difficult to be visually recognized or could not be visually recognized.

<Production of Refrigerant Substance and Refrigerant Pack, and Evaluation of Refrigerant Substance>

Examples 18 to 30

Refrigerant substances and refrigerant packs were produced in the same manner as Example 1 except that the blending components and the concentrations of the refrigerant substance were set as shown in Tables 7 and 8, and the refrigerant substance was evaluated.

Evaluation of the refrigerant substance was performed only for the color change by visual observation. The results are shown in Table 9. In addition, pH (C) of the refrigerant substance is also shown in Table 9.

For example, in Example 18, as an inorganic salt, three types of potassium sulfate, sodium sulphate, and diammonium hydrogen phosphate were used in combination, and the content in the refrigerant substance and as the concentration in the aqueous solution at the time of pH (A) measurement, potassium sulfate was 5% by mass, sodium sulfate was 3% by mass, and diammonium hydrogen phosphate was 2% by weight. In addition, in Example 18, pH (B) was 3.5, and pH (C) was 6.4.

In all of the refrigerant substances of Examples 18 to 30, the inorganic salt was completely dissolved before freezing, but the total amount or almost total amount of the inorganic salt was precipitated after freezing.

In addition, in all of Examples 18 to 30, the content of the pH indicator of the refrigerant substance was 10 ppm.

TABLE 7

| | Blending component | | | | | |
|---|---|---|---|---|---|---|
| | Inorganic salt | | Thickener | | pH indicator | |
| | Name | pH (A) (% by mass) | Name | pH (B) (% by mass) | Name | Color change range (color change) |
| Example 18 | Potassium sulfate<br>Sodium sulfate<br>Diammonium hydrogen phosphate | 7.7<br>(5)<br>(3)<br>(2) | Acryl-based polymer (6) | 3.5 (0.8) | BCP | 5.2 to 6.8 (yellow → violet) |
| Example 19 | Potassium sulfate<br>Sodium sulfate<br>Diammonium hydrogen phosphate | 7.7<br>(5)<br>(3)<br>(2) | Acryl-based polymer (1) | 5.2 (1.3) | BCP | 5.2 to 6.8 (yellow → violet) |
| Example 20 | Potassium sulfate<br>Sodium sulfate<br>Dipotassium hydrogen phosphate | 8.7<br>(5)<br>(3)<br>(2) | Acryl-based polymer (6) | 3.5 (1.3) | BCP | 5.2 to 6.8 (yellow → violet) |
| Example 21 | Potassium sulfate<br>Sodium sulfate<br>Disodium hydrogen phosphate | 8.7<br>(5)<br>(3)<br>(2) | Acryl-based polymer (1) | 5.2 (1.3) | BCP | 5.2 to 6.8 (yellow → violet) |
| Example 22 | Sodium sulfate<br>Dipotassium hydrogen phosphate | 8.8<br>(3)<br>(2) | Acryl-based polymer (1) | 5.2 (1.3) | BCP | 5.2 to 6.8 (yellow → violet) |
| Example 23 | Potassium sulfate<br>Dipotassium hydrogen phosphate | 8.8<br>(3)<br>(2) | Acryl-based polymer (1) | 5.2 (1.3) | BCP | 5.2 to 6.8 (yellow → violet) |

TABLE 8

| | Blending component | | | | | |
|---|---|---|---|---|---|---|
| | Inorganic salt | | Thickener | | pH indicator | |
| | Name | pH (A) (% by mass) | Name | pH (B) (% by mass) | Name | Color change range (color change) |
| Example 24 | Potassium sulfate<br>Sodium chloride<br>Dipotassium hydrogen phosphate | 8.6<br>(5)<br>(3)<br>(2) | Acryl-based polymer (1) | 5.2 (1.3) | BCP | 5.2 to 6.8 (yellow → violet) |
| Example 25 | Sodium chloride<br>Diammonium hydrogen phosphate | 7.7<br>(5)<br>(2) | Acryl-based polymer (1) | 5.2 (1.3) | BCP | 5.2 to 6.8 (yellow → violet) |
| Example 26 | Potassium chloride<br>Sodium sulfate<br>Dipotassium hydrogen phosphate | 8.6<br>(5)<br>(3)<br>(2) | Acryl-based polymer (1) | 5.2 (1.3) | BCP | 5.2 to 6.8 (yellow → violet) |
| Example 27 | Diammonium hydrogen phosphate | 7.9 (5) | Acryl-based polymer (1) | 5.2 (1.3) | BCP | 5.2 to 6.8 (yellow → violet) |
| Example 28 | Diammonium hydrogen phosphate | 7.9 (10) | Acryl-based polymer (1) | 5.2 (1.3) | BCP | 5.2 to 6.8 (yellow → violet) |
| Example 29 | Diammonium hydrogen phosphate | 7.9 (10) | Acryl-based polymer (6) | 3.5 (1.3) | BCP | 5.2 to 6.8 (yellow → violet) |
| Example 30 | Disodium hydrogen phosphate | 9.1 (10) | Acryl-based polymer (1) | 3.5 (1.3) | BCP | 5.2 to 6.8 (yellow → violet) |

TABLE 9

| | pH (C) | Color change |
|---|---|---|
| Example 18 | 6.4 | A (yellow → violet) |
| Example 19 | 6.4 | A (yellow → violet) |
| Example 20 | 6.6 | A (yellow → violet) |
| Example 21 | 6.6 | A (yellow → violet) |
| Example 22 | 6.8 | A (yellow → violet) |
| Example 23 | 6.7 | A (yellow → violet) |
| Example 24 | 6.7 | A (yellow → violet) |
| Example 25 | 6.4 | A (yellow → violet) |
| Example 26 | 6.7 | A (yellow → violet) |
| Example 27 | 6.8 | A (yellow → violet) |

TABLE 9-continued

| | pH (C) | Color change |
|---|---|---|
| Example 28 | 7 | A (yellow → violet) |
| Example 29 | 6.8 | A (yellow → violet) |
| Example 30 | 8.5 | A (yellow → violet) |

As is apparent from the above results, in Examples 18 to 30, with the precipitation of the inorganic salt at the time of freezing, the change in coloring of the pH indicator was reflected, and thus, the color of the refrigerant substance changed clearly, and the cooling state could be easily visually recognized

INDUSTRIAL APPLICABILITY

The present invention can be utilized as a refrigerant pack for various fresh products.

The invention claimed is:

1. A refrigerant pack, comprising:
a refrigerant substance containing water, a precipitating component, a non-precipitating component, and a pH indicator,
wherein the precipitating component precipitates when the refrigerant substance freezes and is a component not corresponding to the pH indicator,
the non-precipitating component does not precipitate when the refrigerant substance freezes and is a component not corresponding to the pH indicator, and
before and after freezing, a change or presence/absence of coloring in the pH indicator is reflected, and the refrigerant substance changes in color.

2. The refrigerant pack according to claim 1,
wherein the precipitating component is an inorganic salt, and the non-precipitating component is a thickener.

3. The refrigerant pack according to claim 1,
wherein, in the refrigerant substance, $a^*$ or $b^*$ in an $L^*a^*b^*$ color system before and after freezing changes from a positive value to a negative value or from a negative value to a positive value, or a difference obtained by subtracting $a^*$ before freezing from $a^*$ after freezing becomes 10 or greater.

4. The refrigerant pack according to claim 1,
wherein, in the refrigerant substance, the content of the precipitating component is 0.1% to 12% by mass, the content of the non-precipitating component is 0.1% to 10% by mass, and the content of the pH indicator is 1 to 30 ppm.

5. The refrigerant pack according to claim 1,
wherein the precipitating component is one or more types selected from the group consisting of hydrochlorides, sulfates, nitrates, carbonates, hydrogenphosphates, hydrogencarbonates, phosphates, chlorides of alkali metals, and chlorides of alkali earth metals.

6. The refrigerant pack according to claim 1,
wherein the non-precipitating component is one or more types selected from the group consisting of an acryl-based polymer, carboxyalkyl cellulose, xanthan gum, guar gum, and hydroxyalkyl guar gum.

* * * * *